US00PP29468P3

(12) United States Plant Patent
Brazelton et al.

(10) Patent No.: US PP29,468 P3
(45) Date of Patent: Jul. 10, 2018

(54) BLUEBERRY PLANT NAMED 'FCM12-045'

(50) Latin Name: ***Vaccinium corymbosum* hybrid**
Varietal Denomination: FCM12-045

(71) Applicant: Fall Creek Farm & Nursery, Inc., Lowell, OR (US)

(72) Inventors: David M. Brazelton, Walterville, OR (US); Adam L. Wagner, Eugene, OR (US); Peter Stefan Boches, Eugene, OR (US); Antonio A. Alamo Bermudo, Seville (ES)

(73) Assignee: Fall Creek Farm & Nursery, Inc., Lowell, OR (US)

( * ) Notice: Subject to any disclaimer, the term of this patent is extended or adjusted under 35 U.S.C. 154(b) by 0 days.

(21) Appl. No.: 15/330,402

(22) Filed: Sep. 15, 2016

(65) Prior Publication Data

US 2017/0099756 P1 Apr. 6, 2017

Related U.S. Application Data

(60) Provisional application No. 62/284,537, filed on Oct. 2, 2015.

(51) Int. Cl.
*A01H 5/08* (2018.01)

(52) U.S. Cl.
USPC ..... Plt./157

(58) Field of Classification Search
USPC ..... Plt./156, 157
See application file for complete search history.

*Primary Examiner* — Susan McCormick Ewoldt
(74) *Attorney, Agent, or Firm* — Hahn Loeser & Parks, LLP

(57) ABSTRACT

The new blueberry plant variety 'FCM12-045' is provided. 'FCM12-045' is a commercial variety intended for the hand harvest fresh market. The new blueberry plant originated from a cross of 'FF-128' (female parent, unpatented) by 'ZF04-002' (pollen parent, unpatented), selected because it flowered and fruited more than most genotypes in a low latitude, zero chill evergreen production system and had larger fruit than the commercial variety Biloxi with a small picking scar.

7 Drawing Sheets

Latin name of the genus, and species:
Genus—*Vaccinium.*
Species—*corymbosum* hybrid.
Variety denomination: The new blueberry plant claimed is of the variety denominated 'FCM12-045'.

STATEMENT REGARDING FEDERALLY-SPONSORED RESEARCH AND DEVELOPMENT

None.

BACKGROUND OF THE INVENTION

The present invention relates to the discovery of a new and distinct cultivar of southern highbush blueberry (*Vaccinium corymbosum* L. hybrid) plant, referred to as 'FCM12-045', as herein described and illustrated. The new blueberry plant variety 'FCM12-045' was selected near Colima City, state of Colima, Mexico in 2012. 'FCM12-045' is a commercial variety intended for the hand harvest fresh market. The variety has high vigor, ripens at the same time as the variety 'Biloxi'(not patented), and produces a medium to large berry with good firmness, and a small picking scar on fruit derived from the current season's growth. 'FCM12-045' was selected for use in an evergreen production system in areas where zero effective chilling hours may be accumulated. The growing region of Colima, Mexico where 'FCM12-045' was originally selected is at a low latitude (~19.5° N) with a sub-tropical climate. In this region, temperatures rarely fall below 45° F. (the maximum temperature at which blueberry buds accumulate chill units to break dormancy) and day lengths only vary from between 10.8 hours in December to 13.2 hours in June. Under these conditions, many traditional low-chill blueberry varieties (developed in latitudes 25°-35°) do not produce flower buds or flowers. In the case of blueberry varieties that do flower under these conditions, the flowers are produced primarily on the current season's growth that is often referred to as a 'primocane' in the blueberry industry. The 'primocane' inflorescences tend to be very elongated in form compared to the inflorescence produced at higher latitudes from dormant buds, and the fruit often does not abscise well from the pedicel, resulting in a large picking scar which greatly limits shelf life. The blueberry industry in this area is dominated by the variety 'Biloxi' (not patented). 'Biloxi' (not patented) is one of the few traditional low chill varieties that grows well and produces fruit with a good picking scar in this growing environment. However, 'Biloxi' (not patented) often produces an excessive proportion of small, unmarketable fruit. 'FCM12-045' was exceptional because it flowered and fruited more than most genotypes but also had larger fruit than Biloxi (not patented) with a small picking scar. 'FCM12-045' also produces significant numbers of flower buds in a zero chill climate, resulting in a harvest window that is more concentrated than 'Biloxi' (not patented), which fruits more heavily on primocanes.

SUMMARY OF THE INVENTION

Pedigree and History: The new blueberry plant originated from a cross of 'FF-128' (female parent, unpatented) by 'ZF04-002' (pollen parent, unpatented).

The cross that produced 'FCM12-045' (denominated by the cross code 'X08-128') was made in Lowell, Oreg., USA in 2008.

The new blueberry plant variety 'FCM12-045' was initially propagated by softwood cuttings in 2012 in Lowell, Oreg., USA. Rooted plants from these cuttings were field planted in Tala, Jalisco, Mexico and also shipped to Lowell, Oreg., USA in 2013. Additional plants have been propagated via softwood cuttings from the plants established in Tala, Mexico in 2014. The plants sent to Lowell, Oreg. were also propagated via softwood cuttings in 2014 and successfully used to establish in vitro culture lines in 2014.

The seedling family that produced 'FCM12-045' was initially grown in 50 cell propagation trays and shipped to Mexico in March, 2011 after the plants had reached sufficient size to be field planted. They were planted in a commercial blueberry field near Colima City, state of Colima, Mexico and evaluated for fruit production and quality beginning in December 2011. 'FCM12-045' was selected in 2012 because it was very vigorous, high yielding, highly evergreen, and had a very concentrated ripening period in an evergreen, zero chill production system. After being selected in Colima, 'FCM12-045' was propagated by softwood cuttings and a ten plant plot was established in Tala, Mexico (near Guadalajara). The ten plant plot was evaluated for fruit quality and yield in comparison to the standard varieties 'Biloxi' (not patented) and 'Ventura' (U.S. Pat. No. 24,606) beginning in December, 2013. After two harvest seasons of evaluation, the yield and fruit quality of 'FCM12-045' were deemed sufficiently good to warrant launching it as a commercial variety.

The new blueberry plant 'FCM12-045' as it grows in Tala, Mexico is distinguished by a highly branched growth habit, with narrowly spaced internodes, and highly evergreen leaves resulting in a rounded plant shape. The new blueberry plant 'FCM12-045' has new leaves that are often reddish-orange in hue and very broadly elliptic or even round in shape, urceolate flowers, and firm, large fruit with a moderately dark color and flattened shape. The new blueberry plant 'FCM12-045' consistently produces larger fruit than the standard variety 'Biloxi' (not patented), which is a very desirable characteristic.

Plants of 'FCM12-045' propagated from softwood cuttings or in vitro are phenotypically stable and exhibit the same characteristics as the original plant. The parents 'FF-128' (not patented) and 'ZF04-002' (not patented) have not been evaluated in the same environment of Mexico that 'FCM12-045' was selected in. In California, USA 'FF-128' (not patented) was discarded after one season of evaluation because it did not grow well there. We have very few other notes of the parent 'FF-128' (not patented) except the original selection notes for it from Lowell, Oreg. where it was noted that it had a concentrated ripening period and firm fruit. The parent 'ZF04-002' has been much more extensively evaluated. The parent 'ZF04-002' is similar to the new blueberry plant 'FCM12-045' in that it is very evergreen, with a highly branched growth habit and short intemodes. However, the leaves of 'FCM12-045' are much more rounded at the apex than leaves of the parent 'ZF04-002' which have an acute apex. The fruit of 'FCM12-045' is similar in shape to the parent 'ZF04-002' but fruit of 'ZF04-002' have a much heavier bloom resulting a lighter blue color than 'FCM12-045'.

DETAILED BOTANICAL DESCRIPTION

Figure 1:
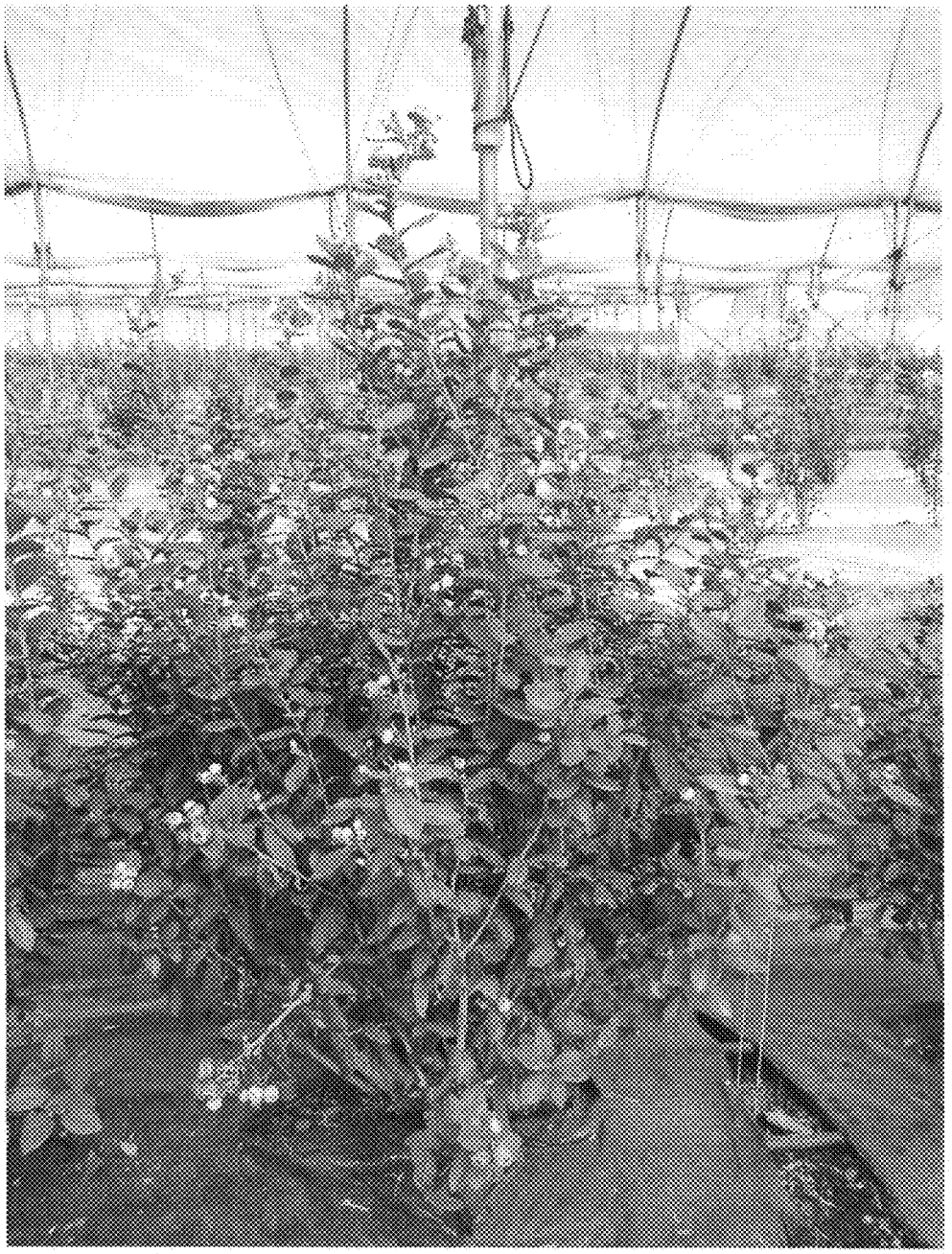
FIG. 1 is a photograph of a mature plant of 'FCM12-045' grown in Tala, Jalisco, Mexico and photographed on Dec. 16, 2015.
Figure 2:
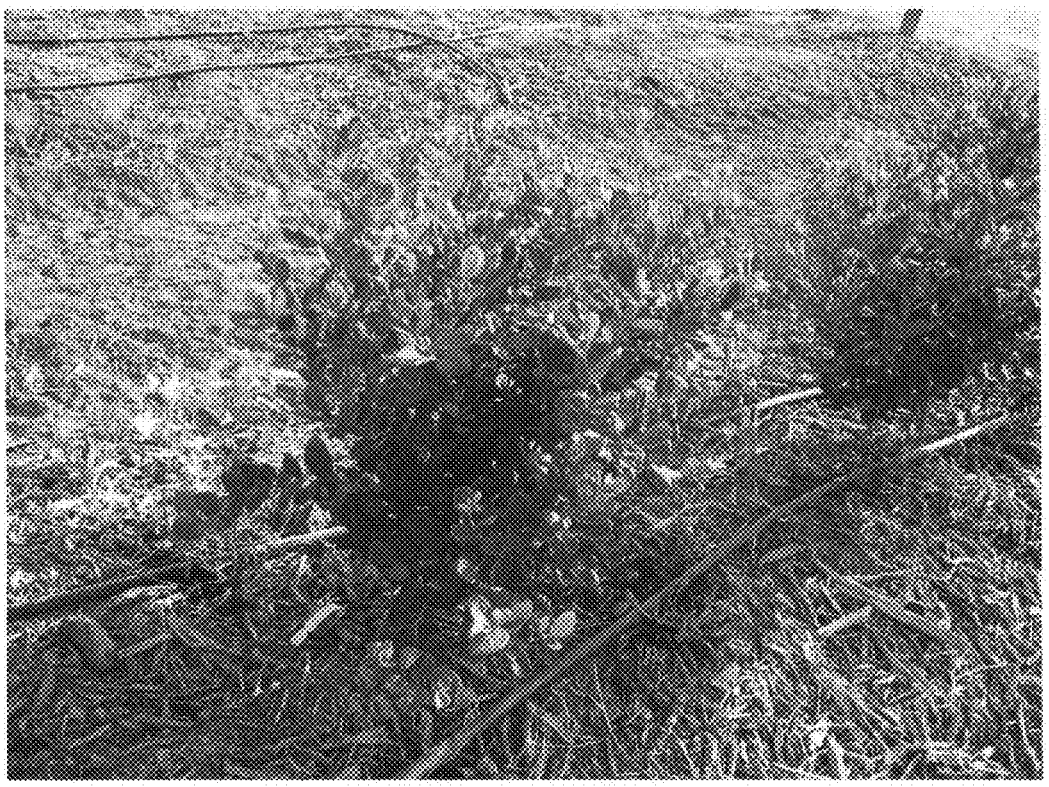
FIG. 2 is a photograph of a young plant of 'FCM12-045' grown in Delano, Calif. and photographed on May 7, 2015.
Figure 3:
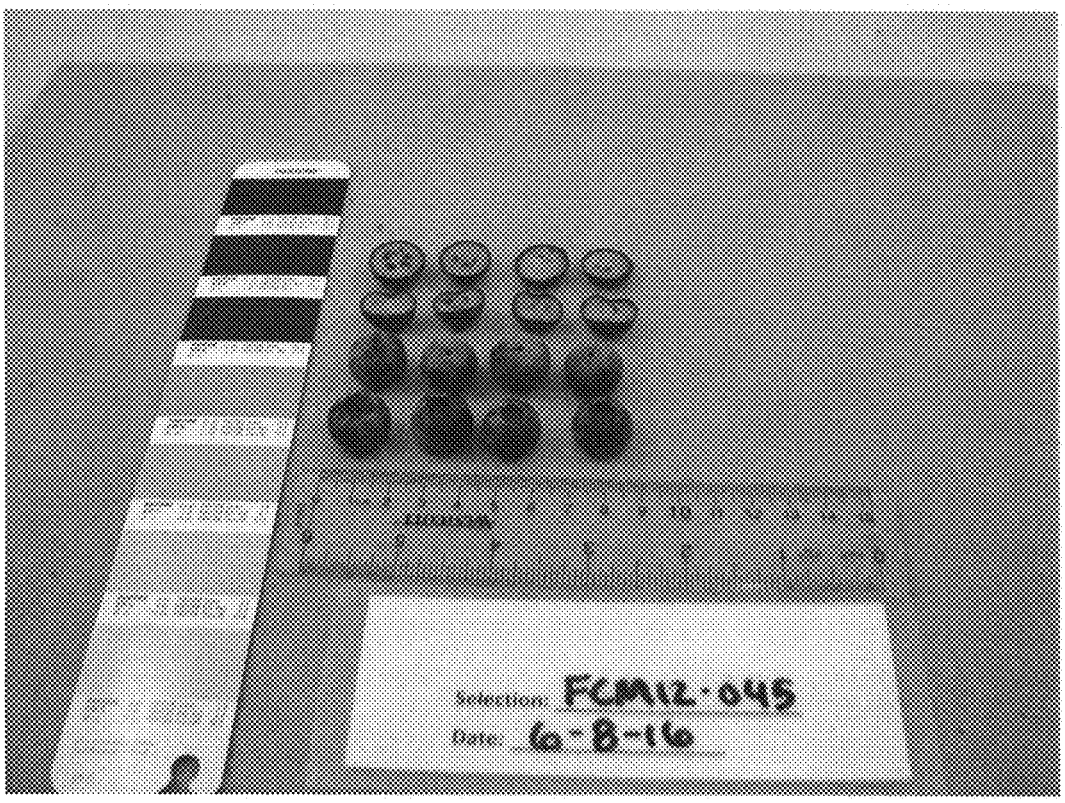
FIG. 3 is a photograph of fruit of 'FCM12-045' grown in Lowell, Oreg. and photographed on Jun. 8, 2016.
Figure 4:
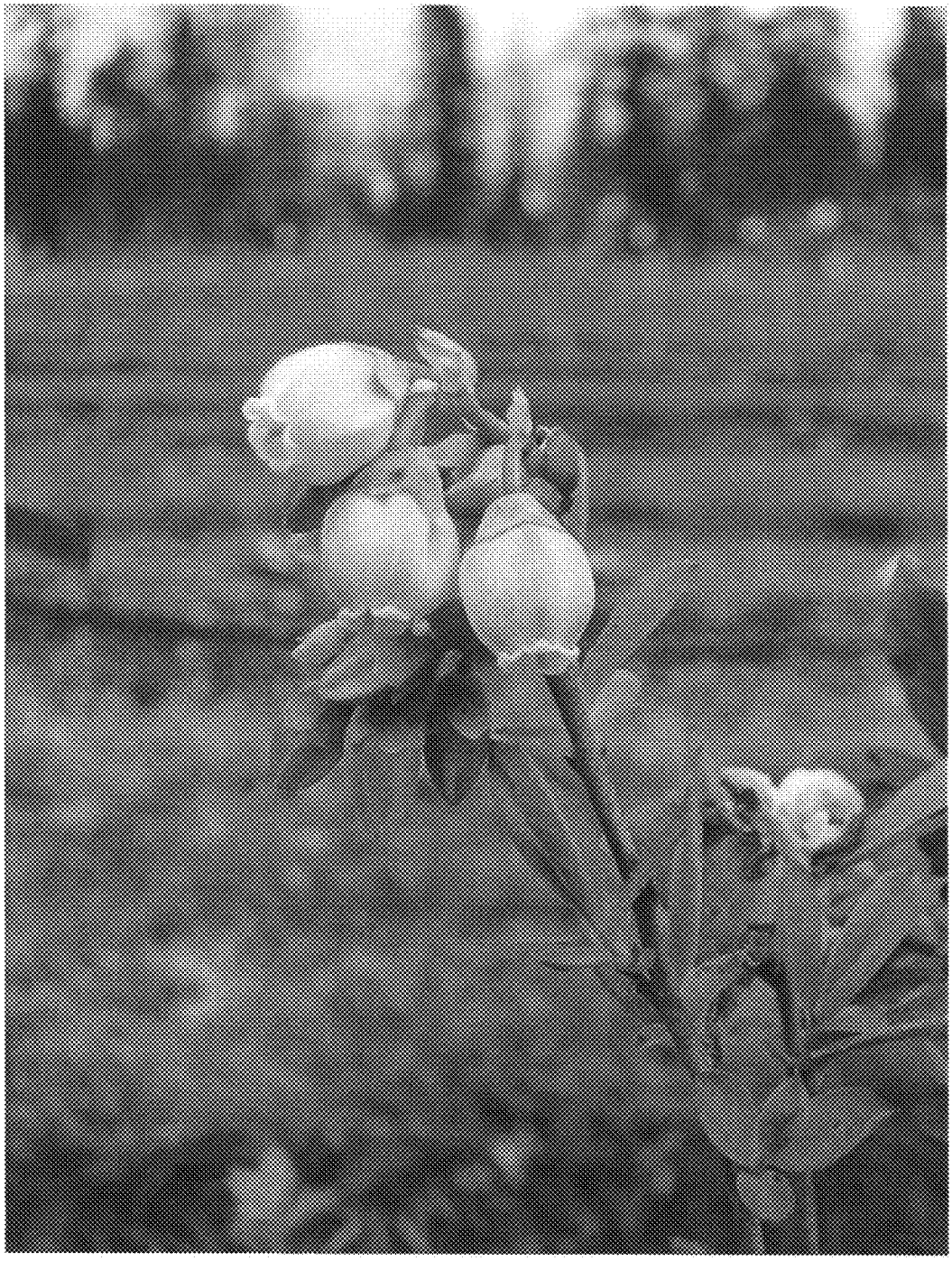
FIG. 4 is a photograph of flowers of 'FCM12-045' grown in Lowell, Oreg. and photographed on Mar. 23, 2016.
Figure 5:
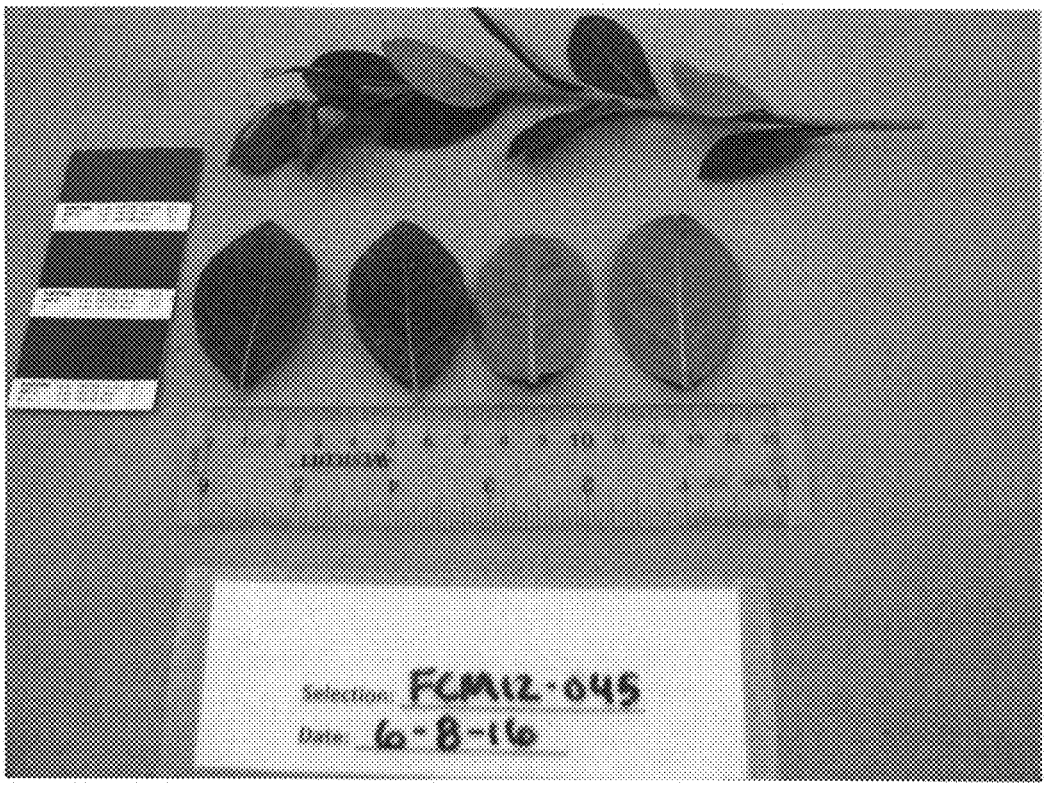
FIG. 5 is a photograph of leaves and young shoot of 'FCM12-045' grown in Lowell, Oreg. and photographed on Jun. 8, 2016.
Figure 6:
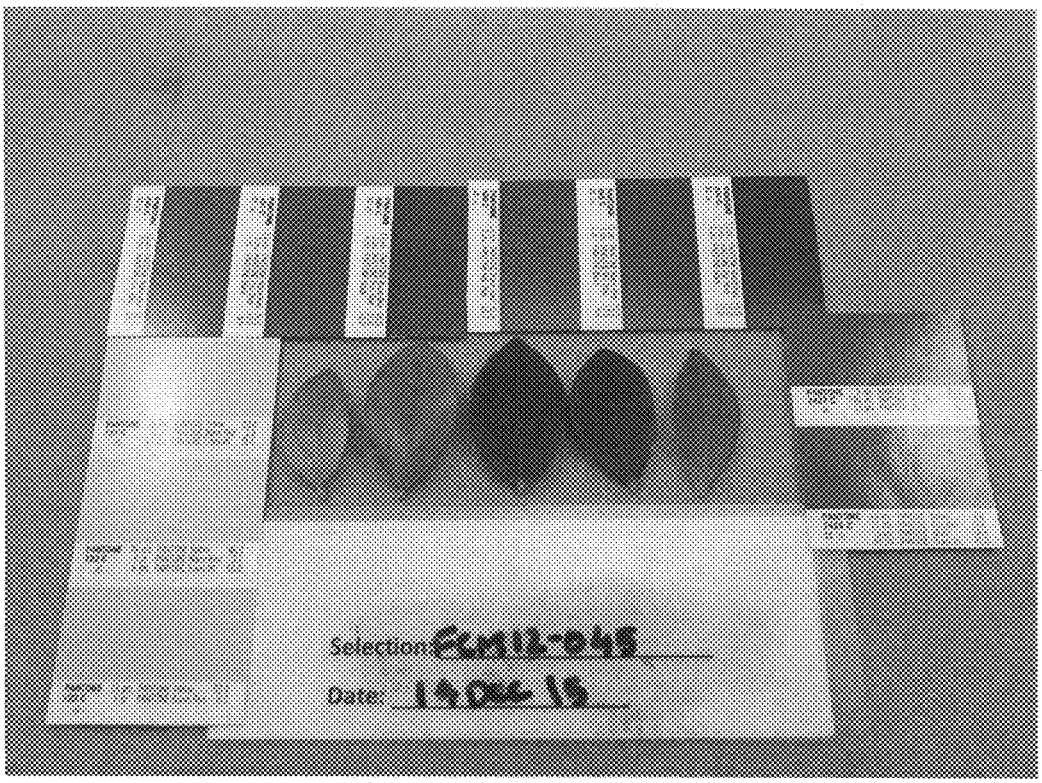
FIG. 6 is a photograph of leaves of 'FCM12-045' grown in Lowell, Oreg. and photographed on Dec. 15, 2015 showing fall color.
Figure 7:
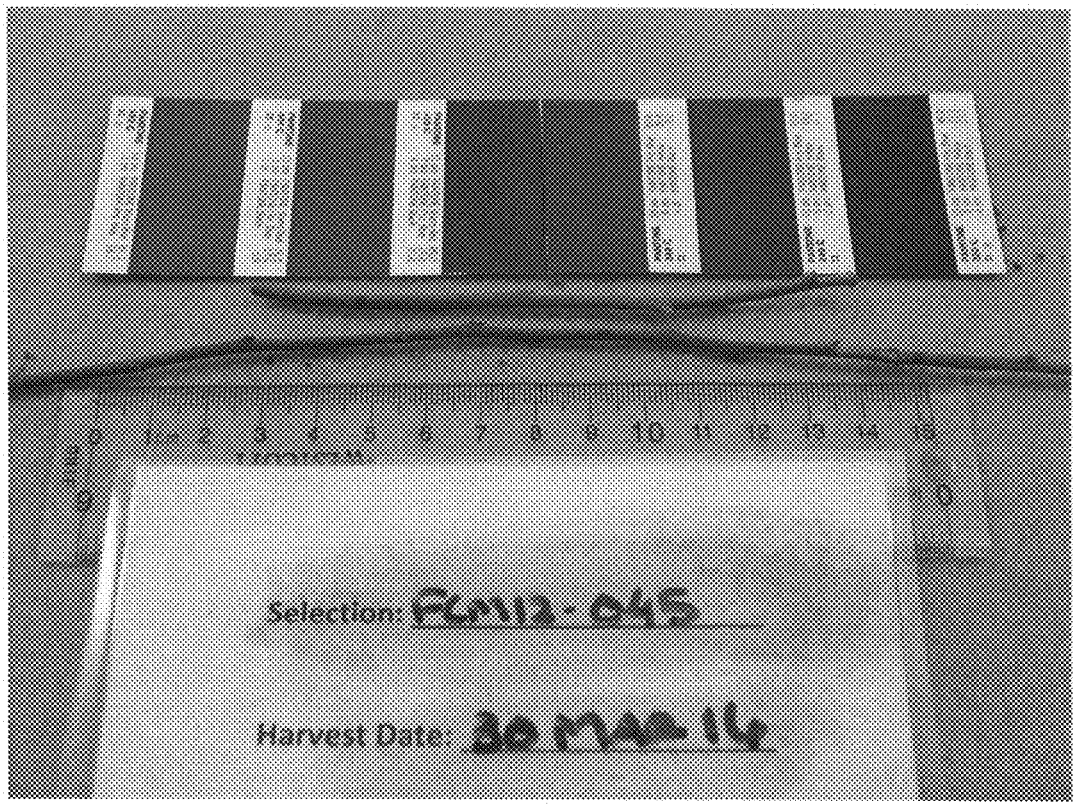
FIG. 7 is a photograph of stems of 'FCM12-045' grown in Lowell, Oreg. and photographed on Mar. 31, 2016.

The following detailed description sets forth the distinctive characteristics of 'FCM12-045'. The data which defines these characteristics was collected from asexual reproductions of the original selection. Dimensions, sizes, colors, and other characteristics are approximations and averages set forth as accurately as possible. All measurements are the average of five observations. The plant history was taken on mature plants approximately 2 years of age, and the descriptions relate to plants grown in the field in Tala, state of Jalisco, Mexico unless otherwise noted (observations on fall leaf color and some other traits were collected on plants grown in Lowell, Oreg.). Descriptions of fruit characteristics were made on fruit grown in Tala, State of Jalisco, Mexico. Color designations are from "The Pantone Book of Color" (by Leatrice Eiseman and Lawrence Herbery, Harry N. Abrams, Inc., Publishers, New York 1990) unless noted otherwise. Where the Pantone color designations differ from the colors in the photographs, the Pantone colors are accurate.

VARIETY

Classification:

a. *Family*.—Ericaceae.
b. *Genus*.—*Vaccinium*.
c. *Species*.—*Corymbosum*.
d. *Common name*.—Southern Highbush Blueberry.

Parentage:

a. *Female parent*.—'FF-128' (not patented).
b. *Male parent*.—'ZF04-002' (not patented).

Market class: Commercial blueberry variety intended for the hand harvest fresh market.

PLANT

General:

a. *Parentage*.—Female parent 'FF-128' (unpatented) Male parent 'ZF04-002' (unpatented).
b. *Plant height*.—Average of 110 cm.
c. *Plant width*.—Average of 116 cm.
d. *Growth habit*.—Erect.

e. *Growth*.—Vigorous.
f. *Productivity*.—Excellent, average of 3.30 kilos per plant, per season on a 2 year old plant, compared to 1.86 kilos per plant per season for the commercial variety 'Biloxi' (not patented).
g. *Cold hardiness*.—Not determined, likely USDA zone 7 given southern highbush parentage.
h. *Chilling requirement*.—Not determined, estimated at less than 700 hours less than 45 degrees Fahrenheit. Capable of fruiting well with zero chill hours when maintained in an evergreen state of growth.
i. *Leafing*.—Excellent leafing.
j. *Twigginess*.—Very twiggy.
k. *Resistance/susceptibility to root rot* (*phytopthora cinnamomii*).—Does not appear to be overly susceptible.
l. *Resistance/susceptibility to stem blight* (*botryosphaeria sp*.).—Does not appear to be overly susceptible.
m. *Resistance/susceptibility to phomopsis twig blight* (*phomopsis vaccinii*).—Not evaluated.
n. *Resistance/susceptibility to botrytis* (*botrytis cinerea*).—Does not appear to be overly susceptible.
o. *Resistance/susceptibility to leaf spot* (*septoria spp*.).—Does not appear to be overly susceptible.
p. *Resistance/susceptibility to leaf rust* (*naohidemyces vaccinii*).—Moderately susceptible to leaf rust.
q. *Resistance/susceptibility to bud mites* (*acalatus vaccinii*).—Not evaluated.

STEM

General:
a. *Suckering tendency*.—High.
b. *Mature cane color*.—Spinach green 16-0439.
c. *Mature cane length*.—Average of 55 cm.
d. *Mature cane width*.—Average of 19.46 mm on a two year old plant.
e. *Bark texture*.—Rough.
f. *Fall color on new shoots*.—Not observed in Tala, Mexico. Pantone colors Green Oasis 15-0538 and Barn Red 18-1531in Lowell, Oreg.
g. *Surface texture of new wood*.—Smooth.
h. *Internode length on strong, new shoots*.—Average of 16.2 mm.
i. *Average number of buds per fruiting lateral*.—Average of 5.8.

FOLIAGE

General:
a. *Time of beginning of leaf bud burst*.—Not observed in Tala, Mexico. In Lowell, Oreg., late February to early March.
b. *Leaf color* (*top side*).—Pantone color Chive 19-0323.
c. *Leaf color* (*under side*).—Pantone colors Mistletoe 16-0220 to Nile 14-0223.
d. *Fall leaf color*.—Not observed in Tala, Mexico. In Lowell, Oreg. Pantone colors Banana 13-0947, Barn Red 18-1531, Red Earth 18-1444, Fiery Red 18-1664, True Red 19-1664, Chinese Red 19-1606, Burgundy 19-1617, and Chive 19-0323.
e. *Leaf arrangement*.—Alternate.
f. *Leaf shape*.—Broadly elliptic.
g. *Leaf margins*.—Entire.
h. *Leaf venation*.—Pinnate.
i. *Leaf apices*.—Obtuse to rounded.
j. *Leaf bases*.—Obtuse.
k. *Leaf length*.—Average of 55.6 mm.
l. *Leaf width*.—Average of 33.0 mm.
m. *Leaf length/width ratio*.—1.68 (medium).
n. *Leaf nectaries*.—Absent.
o. *Pubescence of upper side*.—Absent.
p. *Pubescence of lower side*.—Absent.
q. *Cross sectional profile*.—Slightly revolute.
r. *Longitudinal profile*.—Slightly undulate.
s. *Attitude*.—Erect (acute leaf angle).

Petioles:
a. *Length*.—Average of 3.57 mm.
b. *Width*.—Average of 2.17 mm.
c. *Color*.—Tarragon 15-0326.
d. *Surface texture*.—Smooth.

FLOWERS

General:
a. *Time of beginning of flowering*.—In Tala, Mexico approximately September 15 depending on the timing of the previous pruning. In Lowell, Oreg.: early March.
b. *Time of* 50% *anthesis*.—In Tala, Mexico approximately October 15 depending on timing of the previous pruning. In Lowell, Oreg.: late March.
c. *Flower shape*.—Urceolate.
d. *Flower fragrance*.—Mild, sweet, like Jasmine.
e. *Immature flower color*.—Reed Yellow 13-0915.
f. *Pollen staining*.—95% viable stained with acetocarmine red.
g. *Self-compatibility*.—Excellent, 81.2% of self-pollinated flowers reaching maturity compared to 89% of flowers reaching maturity when pollinated with pollen of 'Biloxi' (not patented).

Corolla:
a. *Color*.—Pantone Antique white 11-0105.
b. *Length*.—Average of 10.78 mm.
c. *Width*.—Average of 8.592 mm.
d. *Aperture width*.—Average of 4.32 mm.
e. *Anthocyanin coloration of corolla at time of anthesis*.—In Tala, Mexico: low. In Lowell, Oreg.: medium.
f. *Corolla ridges*.—Present, distinct.
g. *Protrusion of stigma*.—Average of −0.6 mm below lip of corolla.

Inflorescence:
a. *Color*.—Pantone Antique white 11-0105.
b. *Length*.—Average of 10.78 mm.
c. *Width*.—Average of 8.592 mm.
d. *Aperture width*.—Average of 4.32 mm.
e. *Anthocyanin coloration of corolla at time of anthesis*.—In Tala, Mexico: low. In Lowell, Oreg.: medium.
f. *Corolla ridges*.—Present, distinct.
g. *Protrusion of stigma*.—Average of −0.6 mm below lip of corolla.

Calyx (with sepals):
a. *Diameter*.—Average of 6.5 mm.
b. *Color* (*sepals*).—Pantone Lettuce Green 13-0324.
c. *Calyx surface*.—Smooth.

Stamen:

a. *Length*.—Average of 4.04 mm.

b. *Number per flower*.—10.

c. *Filament color*.—Celery Green 13-0532.

Pistil:

a. *Length*.—Average of 8.52 mm.

b. *Ovary color (exterior)*.—Pantone Spinach green 16-0439.

c. *Style*.—Length — Average of 6.66 mm.

Anther:

a. *Length*.—Average of 3.8 mm.

b. *Number*.—10.

c. *Color*.—Pantone Burnt Orange 16-1448.

Pollen:

a. *Abundance*.—Medium.

b. *Color*.—Pantone Winter White 11-0507.

FRUIT

General:

a. *Time of fruit ripening*.—Approximately October 15 in Tala, Mexico, depending on timing of previous pruning.

b. *Time of 50% maturity*.—Approximately December 5 in Tala, Mexico, depending on timing of previous pruning. In Lowell, Oreg.: June 12.

c. *Fruit development period*.—Approximately 45 days.

d. *Mean harvest date*.—Peak harvest occurred on February 12 in Tala, Mexico when plants were pruned the previous May. Dependent on timing of previous pruning.

e. *Mean date last pick*.—Last pick occurred on May 1 in Tala, Mexico when plants were pruned the previous May. Dependent on timing of previous pruning.

f. *Cluster density*.—Medium.

g. *Berries per cluster*.—Average of 8.4.

h. *Unripe fruit color*.—Pantone Silver Green 12-6204.

i. *Ripe berry color*.—Pantone Purple Impression 17-3919.

j. *Berry skin color after polishing*.—Pantone Dark Navy 19-4013.

k. *Berry surface wax abundance*.—Low.

l. *Berry flesh color*.—Pantone Reed 13-0215.

m. *Berry weight*.—Average of 2.25 g per berry, compared to average of 1.16 g per berry for commercial variety 'Biloxi' (not patented) for fruit grown in Tala, Mexico.

n. *Berry height from calyx to scar*.—Average of 12.86 mm.

o. *Berry diameter*.—Average of 20.42 mm.

p. *Calyx aperture*.—Average of 8.64 mm.

q. *Calyx depth*.—Average of 1.6 mm.

r. *Pedicel length*.—Average of 10.29 mm.

s. *Pedicel surface texture*.—Smooth.

t. *Berry detachment force*.—Medium.

u. *Berry shape*.—Oblong.

v. *Fruit stem scar*.—Small, dry.

w. *Berry flavor*.—Sweet with low acidity.

x. *Sweetness when ripe*.—Medium.

y. *Firmness when ripe*.—High. (1) Acidity when ripe — Low. (2) Storage quality — Excellent. (3) Suitability for mechanical harvesting — Low due to prolonged harvest period. (4) Self-fruitfulness — Excellent. (5) Uses — Fresh market fruit production.

SEED

General:

a. *Seed abundance in fruit*.—Medium.

b. *Seed color*.—Pantone Pecan Brown 17-1430.

c. *Seed dry weight*.—3 mg.

d. *Seed length*.—Average of 2.04 mm.

COMPARISON BETWEEN PARENTAL AND COMMERCIAL CULTIVARS

TABLE 1

Comparison Table

| Denomination of similar variety | Characteristic for comparison | State of expression of similar variety | State of expression of candidate variety (FCM12-045) |
|---|---|---|---|
| FF-128 (not patented) | Plant Vigor | Low | High |
| ZF04-002 (not patented) | Leaf shape | Lanceolate | Elliptic |
| ZF04-002 (not patented) | Fruit: intensity of bloom | high | low |
| Biloxi (not patented) | Leaf shape | Lanceolate | Elliptic |
| Biloxi (not patented) | Leaf margin | Slightly serrate | Entire |
| Ventura (U.S. Plant Pat. No. 24,606) | Fruit: intensity of bloom | High | low |

The invention claimed is:

1. A new and distinct variety of blueberry plant named 'FCM12-045' substantially as illustrated and described herein.

* * * * *